(12) United States Patent
DiLeo et al.

(10) Patent No.: US 8,720,255 B2
(45) Date of Patent: May 13, 2014

(54) WATER UPTAKE MEASUREMENT SYSTEM

(75) Inventors: Gregory DiLeo, Ann Arbor, MI (US); Rameshwar Yadav, Farmington Hills, MI (US); Kevork Adjemian, Birmingham, MI (US)

(73) Assignee: Nissan North America, Inc., Franklin, TN (US)

( * ) Notice: Subject to any disclaimer, the term of this patent is extended or adjusted under 35 U.S.C. 154(b) by 709 days.

(21) Appl. No.: 13/010,095

(22) Filed: Jan. 20, 2011

(65) Prior Publication Data

US 2012/0186664 A1 Jul. 26, 2012

(51) Int. Cl.
*G01N 33/00* (2006.01)
*G01N 5/02* (2006.01)

(52) U.S. Cl.
CPC ............... *G01N 5/025* (2013.01); *G01N 33/00* (2013.01); *G01N 2033/0083* (2013.01)
USPC ................................. 73/73; 73/866; 177/50

(58) Field of Classification Search
CPC ....... G01N 5/025; G01N 19/10; G01N 33/00; G01N 2033/0078; G01N 2033/0083
USPC ............... 73/73–74, 863, 863.11, 865.9–866; 177/50; 429/90
See application file for complete search history.

(56) References Cited

U.S. PATENT DOCUMENTS

| | | | |
|---|---|---|---|
| 6,074,458 A * | 6/2000 | Bittner et al. | ............ 95/60 |
| 6,113,261 A | 9/2000 | Blaine | |
| 7,310,995 B2 | 12/2007 | Dziki | |
| 7,357,045 B2 | 4/2008 | Rasmussen et al. | |

FOREIGN PATENT DOCUMENTS

CN 101738454 A * 6/2010

OTHER PUBLICATIONS

TA Instruments, brochure entitled Thermal Analysis, 2010, 13 pages. (includes pp. 72-89 from unidentified publication).*
TA Instruments, brochure entitled Thermal Analysis, 2012, 14 pages. (includes pp. 56-75 from unidentified publication).*
Majsztrik, Paul W., et al "Water Sorption, Desorption and Transport in Nafion Membranes." Journal of Membrane Science 301(2007): 93-106, available online Jun. 16, 2007.
Miyake, N., et al "Evaluation of a Sol-gel Derived Nafion/Silica Hybrid Membrane for Polymer Electrolyte Membrane Fuel Cell Applications." Jounral of the Electrochemical Society 148.8 (2001):A905-A909, available electronically Jul. 5, 2011.
Yang, C., et al. Water Uptake and Conductivity of Composite Membranes Operating at Reduced Relative Humidity. Princeton: Princeton University, 2002, 1 page.
IGAsorp Product Literature entitled Dynamic Sorption Analysis, Hiden Isochema Ltd., Warrington, England, United Kingdom, 6 pages, by Jan. 2011.
Q5000 SA Product Literature, TA Instruments, Inc., New Castle, Delaware, United States of America, 2009 14 pages selected from 123+ pages.

* cited by examiner

*Primary Examiner* — Thomas P Noland
(74) *Attorney, Agent, or Firm* — Young, Basile, Hanlon & MacFarlane, P.C.

(57) ABSTRACT

A water uptake measurement system for measuring uptake of a fluid by a sample includes a sample chamber, a suspension component and a supply interface. A suspension aperture is located at a first end of the sample chamber and extends from an outer surface of the sample chamber to an inner surface of the sample chamber. The suspension component passes through the suspension aperture and is configured to support the sample within the internal cavity such that the sample is spaced apart from the inner surface of the sample chamber. The supply interface is configured to deliver the fluid to the internal cavity of the sample chamber.

15 Claims, 6 Drawing Sheets

WATER UPTAKE MEASUREMENT SYSTEM

FIELD OF THE INVENTION

The invention relates to the field of devices for measuring water uptake by a sample in a humid environment.

BACKGROUND OF THE INVENTION

Fuel cells efficiently and electrochemically convert fuel into electric current, which may then be used to power electric circuits, such as drive systems for vehicles. Fuel cells typically include an electrolyte substance. One common electrolyte substance that is utilized in fuel cells is a proton-exchange membrane (PEM), such as Nafion, which is often used in fuel cells that are utilized to power vehicles. PEMs function by conducting protons from a fuel source, while at the same time acting as a barrier to electrons from the fuel source. The electrons are rerouted to the electric load of the fuel cell.

Conventional PEMs must remain at a minimum level of hydration in order to remain stable and function desirably. Therefore, when designing PEM fuel cells for use in extreme temperatures or low humidity environments, the water uptake properties of the PEM must be carefully evaluated.

Conventional water uptake measurement systems available in the marketplace are very expensive and cumbersome to operate. Therefore, need remains, especially in the field of PEM evaluation, for a water uptake measurement system that is practical, inexpensive, and allows for control of the temperature and humidity that a sample is exposed to.

SUMMARY OF THE INVENTION

Water uptake measurement systems and methods for measuring uptake of a fluid by a sample are disclosed herein.

One measurement system taught herein has a sample chamber having an outer surface, an inner surface, an internal cavity, and a suspension aperture that is located at a first end of the sample chamber. The suspension aperture extends from the outer surface of the sample chamber to the inner surface of the sample chamber.

The measurement system includes a suspension component that passes through the suspension aperture of the sample chamber such that a first end of the suspension component is located outside of the internal cavity of the sample chamber and a second end of the suspension component is suspended within the internal cavity of the sample chamber. The suspension component is configured to support the sample within the internal cavity such that the sample is spaced apart from the inner surface of the sample chamber.

The measurement system also includes a supply interface that is configured to deliver the fluid to the internal cavity of the sample chamber.

BRIEF DESCRIPTION OF THE DRAWINGS

The description herein makes reference to the accompanying drawings wherein like reference numerals refer to like parts throughout the several views, and wherein.

DETAILED DESCRIPTION OF THE EMBODIMENT

Figure 1:
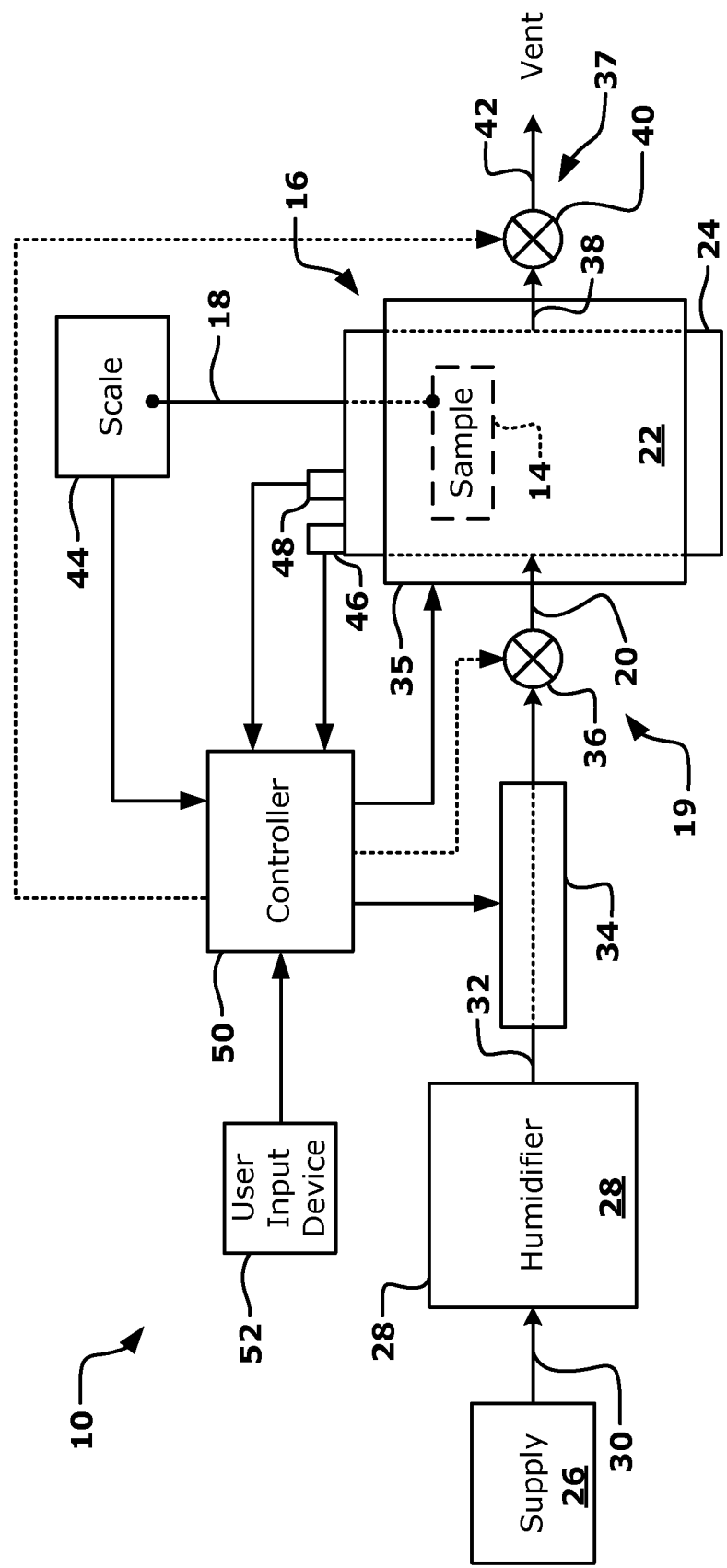
FIG. 1 is a block diagram showing a water uptake measurement system.
Figure 2:
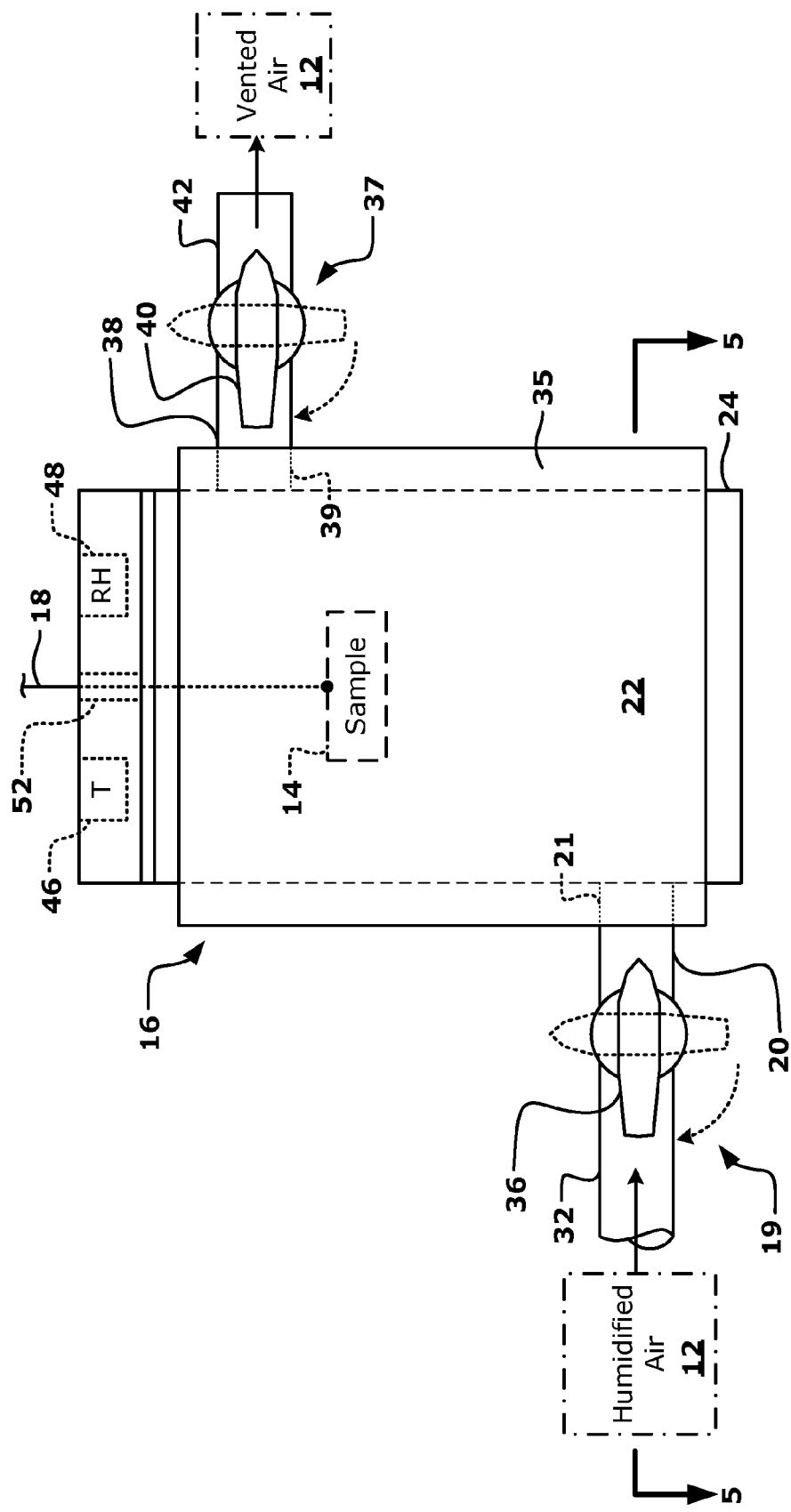
FIG. 2 is a side view showing a sample chamber that is connected to a supply conduit and a vent conduit.
Figure 3:
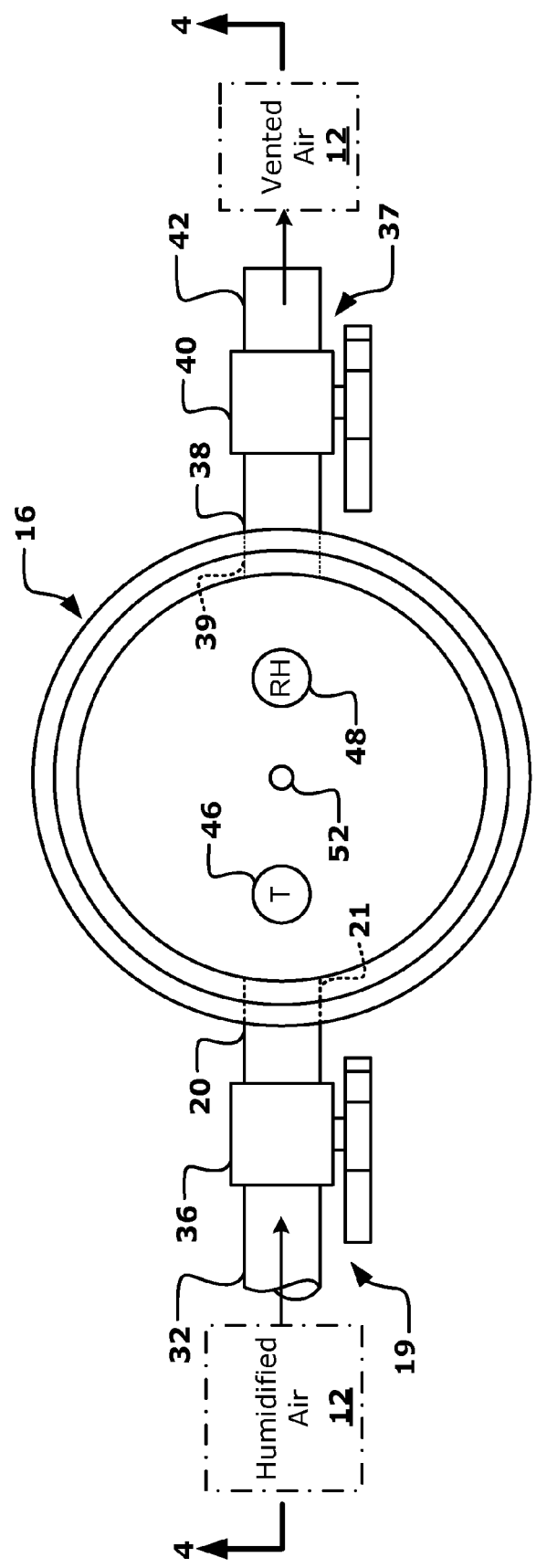
FIG. 3 is a top view of the sample chamber of FIG. 2.

FIGS. 1-3 show a water uptake measurement system 10 according to the invention for measuring uptake of a fluid 12 by a sample 14. The system 10 includes a sample chamber 16, a suspension component 18 for suspending the sample 14 within the chamber 16 and a supply interface 19 that is configured to deliver the fluid 12 to an internal cavity 22 of the sample chamber 16.

As will be described fully herein, the water uptake measurement system 10 is adapted to determine the degree to which the sample 14 has absorbed the fluid 12. The water uptake measurement system 10 will be shown and described herein with reference to measurement of uptake of the fluid 12 in the form of humidified air, water vapor, and/or liquid water by the sample 14 in the form of a polymeric proton exchange membrane, such as Nafion, for use in a fuel cell. However, it should be understood that the water uptake measurement system 10 need not be limited to use with any particular fluid or type of sample, but rather, could be utilized with a broad range of fluids and samples other than those described in the exemplary embodiments herein.

In order to introduce the fluid 12 into the internal cavity 22 of the sample chamber 16, the water uptake measurement system includes the supply interface 19. The supply interface 19 is configured to deliver the fluid 12 to the internal cavity 22 of the sample chamber 16. For example, in this case, the supply interface 19 includes a supply conduit 20, a moisture conduit 32, and a supply valve 36. However, the supply interface 19 is not limited to this particular configuration, but rather, could include any combination of components capable of delivering the fluid 12 to the internal cavity of the sample chamber 16.

The fluid 12 is provided by a fluid supply 26. The fluid supply 26 is in communication with a humidifier 28 by way of one or more fluid conduits 30 in order to deliver the fluid 12 to the humidifier 28. For example, the fluid supply 26 could be configured to supply air at ambient temperature and humidity to the humidifier 28, as well as providing liquid water to the humidifier 28.

The humidifier 28 then processes the fluid 12 supplied to it by the fluid supply 26 in order to convert the fluid 12 into humidified air. The humidifier 28 may process the fluid 12 such that it is brought to a predetermined relative humidity level, or alternatively, the humidifier 28 could be controlled to adjust the relative humidity level of the fluid 12 in real time in response to the conditions within the internal cavity of the sample chamber 16, as will be discussed further herein.

Once the fluid 12 has been humidified, it exits the humidifier 28 and enters the moisture conduit 32 of the supply interface 19. At this point, the fluid 12 could be in the form of humidified air.

The moisture conduit 32 is in communication with the supply valve 36. The supply valve 36 could be an electrically-operated valve that is controlled in order to achieve a desired temperature and relative humidity within the internal cavity 22 of the sample chamber 16, as will be described further herein. Alternatively, the supply valve 36 could be a manually-operated valve. The supply valve 36 is in fluid communication with both the moisture conduit 32 and the supply conduit 20. When the supply valve 36 is in an open position, fluid communication is established between the supply conduit 20 and the moisture conduit 32. When the supply valve 36 is in a closed position (shown in broken lines in FIG. 2), fluid communication between the moisture conduit 32 and the supply conduit 20 is interrupted, such that they are not in fluid communication with one another.

The supply conduit 20 is connected to a base portion 24 of the sample chamber 16 and is in fluid communication with the internal cavity 22 through a supply aperture 21 of the sample chamber 16.

A supply heating element 34 could be provided to regulate the temperature of the fluid 12, and is configured to supply heat to the moisture conduit 32. For example, the supply heating element 34 could be a heat tape that is connected to the moisture conduit 32, such as by wrapping the heating element 34 around the moisture conduit 32. The supply heating element 34 is regulated to achieve a desired temperature within the internal cavity 22 of the sample chamber 16, as will be discussed further herein. In order to further control the temperature within the internal cavity 22 of the sample chamber 16, a chamber heating element 35 could be provided. The chamber heating element 35 could be a heat tape, similar to the supply heating element 34, as will be discussed further herein.

In order to selectively release the fluid 12 from the internal cavity 22 of the sample chamber 16, a vent interface 37 is configured to remove the fluid 12 from the internal cavity 22 of the sample chamber 16. The vent interface 37 is in fluid communication with the internal cavity 22 of the supply chamber 16 through a vent aperture 39. The vent interface 37 includes a vent conduit 38 that is connected to the vent aperture 39, a vent port 42, and a vent valve 40 that selectively establishes and disrupts fluid communication between the vent conduit 38 and the vent port 42.

The vent conduit 38 is connected to the base portion 24 of the sample chamber 16 for fluid communication with the internal cavity 22 of the sample chamber 16. The vent conduit 38 is connected to the vent valve 40. Similar to the supply valve 36, the vent valve 40 could be an electrically-operated valve that is configured to selectively vent the fluid from the internal cavity 22 of the sample chamber 16. Alternatively, the vent valve 40 could be a manually-operated valve. The vent valve 40 is in fluid communication with the vent conduit 38 and the vent port 42. The vent port 42 is operable to vent the fluid 12, typically to atmosphere. The vent valve 40 selectively establishes and disrupts fluid communication between the vent conduit 38 and the vent port 42. When the vent valve 40 is in an open position, fluid communication is established between the vent conduit 38 and the vent port 42. When the vent valve 40 is in a closed position (shown in broken lines in FIG. 2), fluid communication is disrupted between the vent conduit 38 and the vent port 42, such that they are not in fluid communication with one another.

A measuring device such as a scale 44 is provided to determine the degree of water uptake by the sample 14, such as by measuring the mass and/or weight of the sample 14. The scale 44 is connected to the suspension component 18, such that the mass and/or weight of the sample 14 can be determined by the scale 44. The suspension component is configured to transmit the mass and/or weight of the sample 14 to the scale 44. For example, in this case, the suspension component 18 is a line. The suspension component 18 could, however, be a filament, string, rod, or any other member operable to transmit the mass and/or weight of the sample 14 to the scale 44.

In order to permit the suspension component 18 to pass into the internal cavity 22 of the sample chamber 16, the suspension component 18 passes through a suspension aperture 52 that is formed through the sample chamber 16. The suspension aperture 52 has a diameter that is slightly larger than that of the suspension component 18, to minimize temperature and humidity losses from the internal cavity 22.

In order to monitor the temperature within the internal cavity of the sample chamber 16, one or more sensors are provided for detecting a condition within the internal cavity 22 of the sample chamber 16. These sensors could include a temperature sensor 46 and a humidity sensor 48, operation of which will be described in detail herein.

The water uptake measurement system 10 includes a programmable controller 50 that is in electrical communication with the supply heating element 34, the chamber heating element 35, the supply valve 36, the vent valve 40, the scale 44, the temperature sensor 46, and the humidity sensor 48. The programmable controller 50 is conventional in nature, including a processor, memory, inputs, and outputs.

The controller 50 is operable to selectively activate and deactivate each of the supply heating element 34, the chamber heating element 35, the supply valve 36, and the vent valve 40. The controller 50 may also be in electrical communication with the humidifier 28 to selectively activate and deactivate the humidifier 28 and/or adjust an output humidity level for the humidifier 28. The controller 50 is configured to receive input signals from each of the scale 44, the temperature sensor 46, and the humidity sensor 48 representing the mass and/or weight of the sample, the temperature within the internal cavity 22 of the sample chamber 16, and the relative humidity within the internal cavity 22 of the sample chamber 16, respectively. Furthermore, the controller 50 may incorporate or be electrically connected to a user input device 52 for allowing modification of the operating parameters of the water uptake measurement system 10 by a user input.

Figure 4:
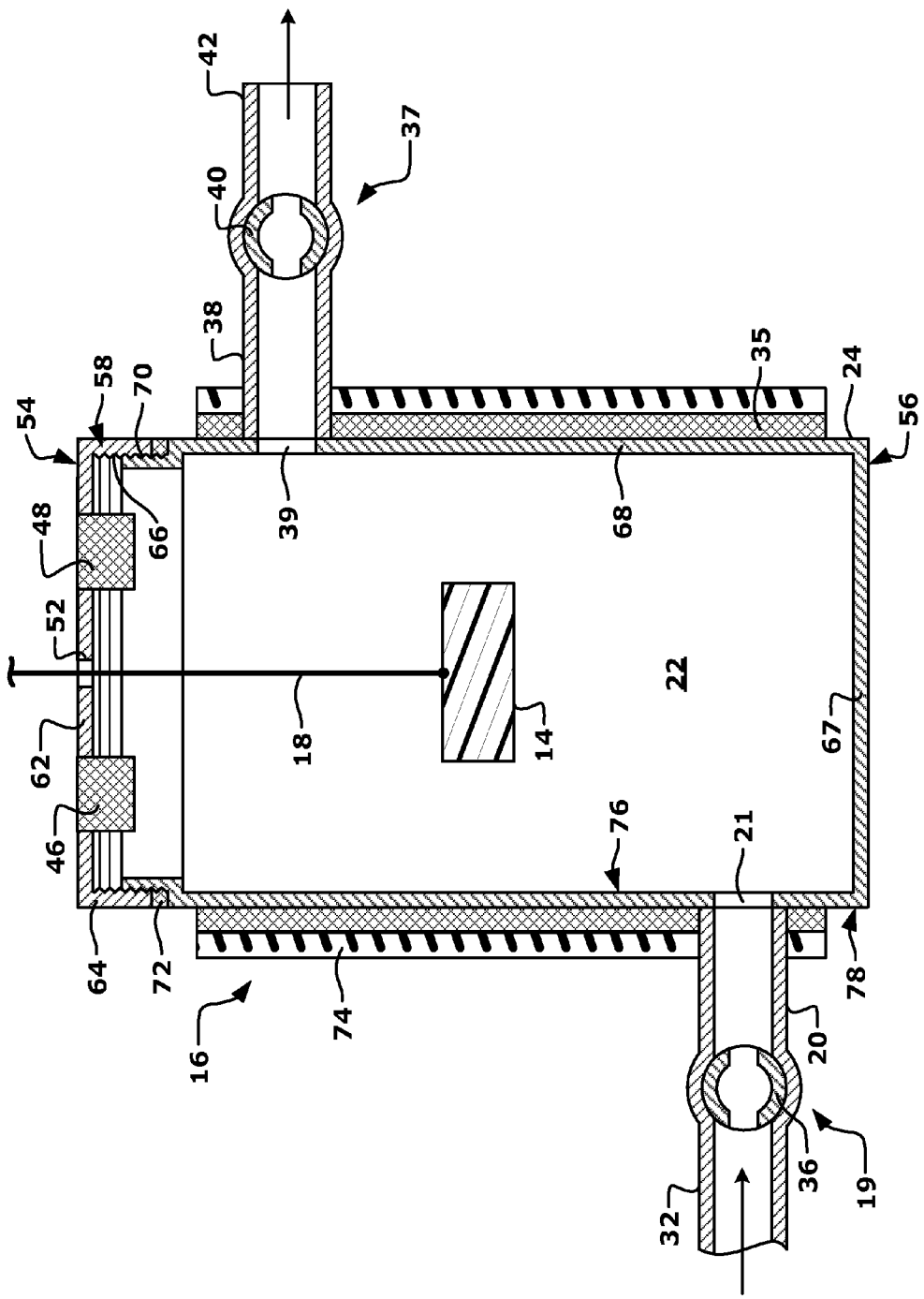
FIG. 4 is a side cross-section view taken along line 4-4 of FIG. 3.
Figure 5:
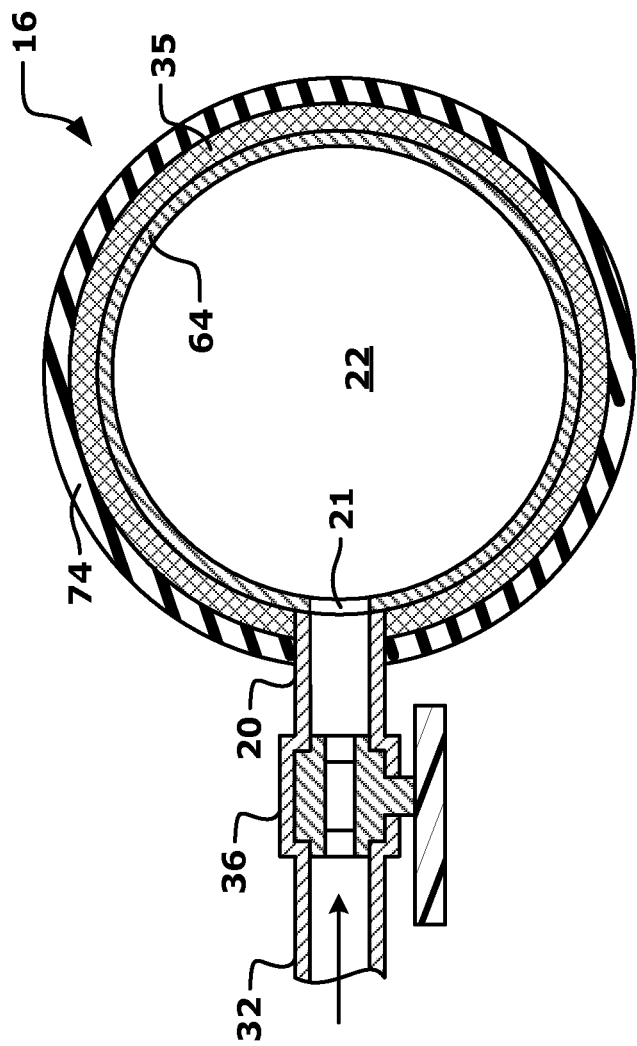
FIG. 5 is a top cross-section view taken along line 5-5 of FIG. 2 showing an interface between the sample chamber and the supply conduit.

As shown in FIGS. 4-5, the sample chamber 16 extends from a first end 54 to a second end 56. As shown in the illustrated embodiment, the first end 54 is an upper end of the sample chamber 16, and the second end 56 is a lower end of the sample chamber 16. Thus, the first end 54 and the second end 56 of the sample chamber 16 are opposite one another. Furthermore, the supply interface 19 can be located adjacent to the second end 56 of the sample chamber 16 and the vent interface 37 can be located adjacent to the first end 54 of the sample chamber 16. In this manner, the fluid 12 is introduced to the sample chamber 16 near its bottom, and the fluid is vented from the sample chamber 16 near its top. Also, the temperature sensor 46 and the humidity sensor 48 could be mounted to the sample chamber 16 at the first end 54. In addition, the suspension aperture 52 could be formed through the sample chamber 16 at the first end 54.

The sample chamber 16 could be a two-part structure that includes a removable portion 58 that is selectively separable from the base portion 24.

The removable portion 58 of the sample chamber 16 could be, for example, a lid-like structure including an end wall 62 and a peripheral wall 64 that extends downward from the periphery of the end wall 62. The temperature sensor 46 and the humidity sensor 48 could be connected to the end wall 62 of the removable portion 58. Additionally the temperature sensor 46 and the humidity sensor 48 could be embedded in the end wall 62 of the removable portion 58 as illustrated in FIG. 4. In this manner, the temperature sensor 46 and the humidity sensor 48 are exposed to the inner cavity 22 of the sample chamber 16 while at the same time being visible from outside of the sample chamber 16 so that an operator can observe readings from the temperature sensor 46 and the humidity sensor 48 in real-time. Of course, the temperature sensor 46 and the humidity sensor 48 can be mounted in any other location on or within the sample chamber 16 as needed and/or desired. The suspension aperture 52 could be formed through the end wall 62 of the removable portion 58. A threaded portion 66 is provided on the interior of the peripheral wall 64 for complementary engagement with the base portion 24 of the sample chamber 16.

The base portion 24 defines the majority of the internal cavity 22 of the sample chamber 16. The base portion 24 includes an end wall 67 and a peripheral wall 68 that extends upward with respect to the end wall 67. The end wall 67 is positioned at the second end 56 of the sample chamber 16. A threaded portion 70 is formed on the exterior of the peripheral wall 68 near the first end 54 of the sample chamber 16. The threaded portion 70 of the base portion 24 is threadedly engageable with the threaded portion 66 of the removable portion 58 of the sample chamber 16. In order to create a seal between the base portion 24 and the removable portion 58 at the interface between their respective threaded portions 66, 70, a gasket 72 could be provided to seal the removable portion 58 with respect to the base portion 24 of the sample chamber 16 when the removable portion 58 is in engagement with the base portion 24 of the sample chamber 16.

The supply aperture 21 could be formed through the peripheral wall 68 of the base portion 24 at the second end 56 of the sample chamber 16, adjacent to the end wall 67 of the base portion 24. The vent aperture 39 could be formed through the peripheral wall 68 of the base portion 24 adjacent to the first end 54 of the sample chamber 16. The vent aperture 39 could be adjacent to the threaded portion 70 of the base portion 24 of the sample chamber 16.

The supply heating element 35 extends around the peripheral wall 68 of the base portion 24. Optionally, the supply heating element 35 could cover the end wall 67 of the base portion 24, or could cover all or part of the removable portion 58 of the sample chamber 16. As discussed in connection with the supply heating element 34, the chamber heating element 35 could be an electrical heat tape or other suitable heating apparatus that is controlled by the controller 50 in order to regulate the temperature within the internal cavity 22 of the sample chamber 16. In order to minimize heat losses, an insulating component such as an insulating layer 74 could be provided on the chamber heating element 35, such that the chamber heating element 35 is interposed between the sample chamber 16 and the insulating layer 74.

From the foregoing, it will be understood that the base portion 24 and the removable portion 58 of the sample chamber 16 cooperate to define an internal surface 76 of the sample chamber 16 that faces the internal cavity 22. It should also be understood that the base portion 24 and the removable portion 58 of the sample chamber 16 cooperate to define an external surface 78 that faces the ambient environment. Furthermore, it should be understood that the chamber heating element 35 is in contact with the external surface 78 of the sample chamber 16. Also, each of the supply aperture 21, the vent aperture 39, and the suspension aperture 52 extend from the external surface 78 to the internal surface 76 of the sample chamber 16.

Operation of the water uptake measurement system 10 will now be explained with reference to FIG. 6. Initially, the sample 14 is placed within the internal cavity 22 of the sample chamber 16, such that it is suspended from the scale 44 by the suspension component 18. The measurement procedure then starts by opening the supply valve 36 in step S101. The operator of the water uptake measurement system 10 is then prompted to input desired temperature and relative humidity parameters using the user input device 52 in step S102. Alternatively, predetermined temperature and relative humidity parameters could be provided to the controller 50 in advance, or previously provided parameters could be stored and reused, thereby eliminating the need for user input.

Next, in step S103, the supply heating element 34 and the chamber heating element 35 are adjusted by the controller 50 in order to meet the desired temperature and relative humidity parameters. Sensor values, such as from the temperature sensor 46 and the humidity sensor 48, are then read in step 104. Based on these readings, it is determined whether or not the desired parameters have been met in step S105. If the parameters have been met, the process proceeds to step S106. If the desired parameters have not been met, the process returns to step S104, where the sensor values are again read. The sensor values will continue to be queried in this manner until the desired temperature and relative humidity parameters have been attained.

In step S106, since the desired temperature and relative humidity parameters have been met, both the supply valve 36 and the vent valve 40 are closed. Then, a delay is imposed in step S107 in order to allow the conditions within the internal cavity 22 of the sample chamber 16 to reach equilibrium. After this delay time has passed, the scale 44 is queried by the controller 50 in step S108 to read the weight and/or mass of the sample 14 using the scale 44. At this time, the vent valve 40 is also opened to vent the internal cavity 22 of the sample chamber 16 to atmosphere, and the process ends.

Figure 6:
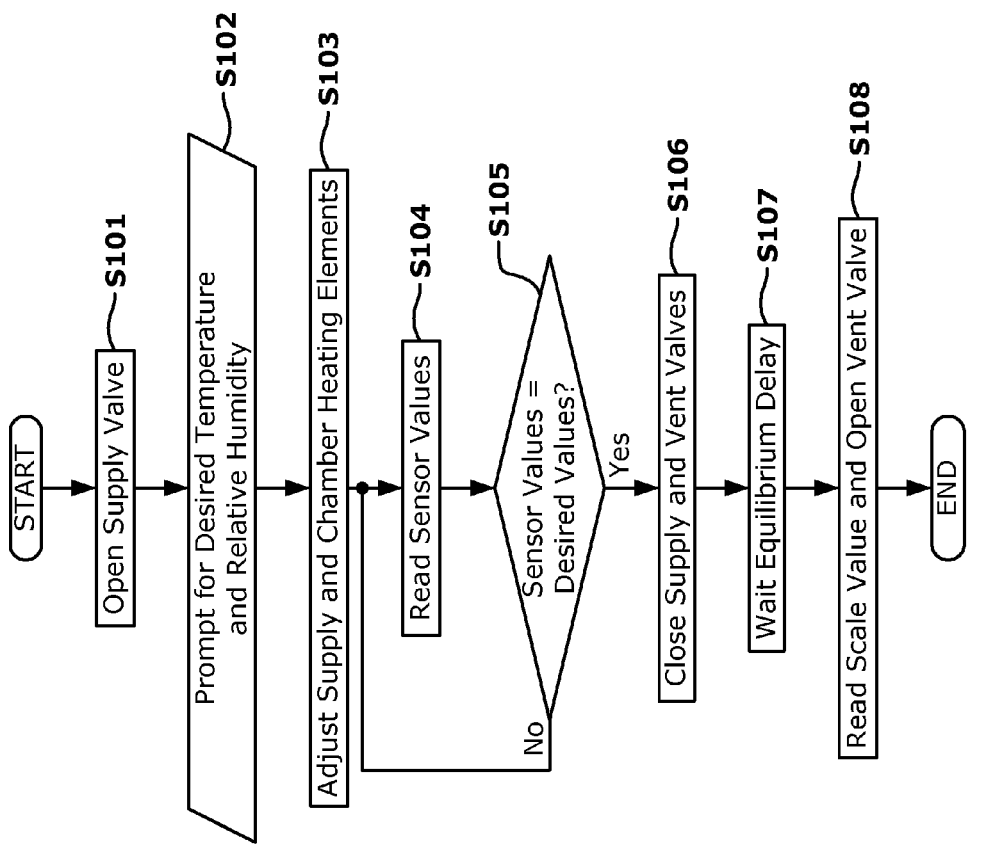
FIG. 6 is a flow chart illustrating steps performed by a controller of the water uptake measurement system during an exemplary water uptake test procedure.

While only a single iteration of a testing procedure is illustrated in FIG. 6, any number of tests may be performed in sequence as needed and/or desired. For example, a test may be executed according to a predetermined duration. This can be based, for example, upon passage of a predetermined period of time and/or upon completion of a predetermined number of iterations. Of course, any other suitable parameters can be employed to determine the duration of the test.

While the invention has been described in connection with what is presently considered to be the most practical and preferred embodiment, it is to be understood that the invention is not to be limited to the disclosed embodiments but, on the contrary, is intended to cover various modifications and equivalent arrangements included within the spirit and scope of the appended claims, which scope is to be accorded the broadest interpretation so as to encompass all such modifications and equivalent structures as is permitted under the law.

What is claimed is:

1. A water uptake measurement system for measuring uptake of a fluid by a sample, comprising:
 a sample chamber having an outer surface, an inner surface, an internal cavity having a controlled temperature and humidity, and a suspension aperture that is located at a first end of the sample chamber, wherein the suspension aperture extends from the outer surface of the sample chamber to the inner surface of the sample chamber;
 a suspension component that passes through the suspension aperture of the sample chamber such that a first end of the suspension component is located in an ambient temperature and humidity area outside of the internal cavity of the sample chamber and a second end of the suspension component is suspended within the internal cavity of the sample chamber, wherein the suspension component is configured to support the sample within the internal cavity such that the sample is spaced apart from the inner surface of the sample chamber, and the suspension aperture is sized and configured to allow the suspension component to pass therethrough and to minimize temperature and humidity losses from the internal cavity to the ambient temperature and humidity area; and a supply interface that is configured to deliver the fluid to the internal cavity of the sample chamber.

2. The water uptake measurement system of claim 1, further comprising:
a vent interface that is configured to remove the fluid from the internal cavity of the sample chamber.

3. The water uptake measurement system of claim 2, wherein the vent interface include a valve that is configured to selectively interrupt flow of the fluid from the internal cavity of the sample chamber.

4. The water uptake measurement system of claim 2, wherein the vent interface is in fluid communication with the internal cavity through a vent aperture located adjacent to the first end of the sample chamber.

5. The water uptake measurement system of claim 1, wherein the supply interface includes a valve that is configured to selectively interrupt flow of the fluid to the internal cavity of the sample chamber.

6. The water uptake measurement system of claim 1, wherein the supply interface is in fluid communication with the internal cavity through a supply aperture located adjacent to a second end of the sample chamber that is located opposite the first end of the sample chamber.

7. The water uptake measurement system of claim 1, further comprising:
a sensor that is mounted to the sample chamber for detecting a condition within the internal cavity.

8. The water uptake measurement system of claim 7, wherein the sensor is mounted at the first end of the sample chamber.

9. The water uptake measurement system of claim 7, wherein the sensor detects at least one of temperature or relative humidity.

10. The water uptake measurement system of claim 1, further comprising:
a heating element that is in contact with the outer surface of the sample chamber.

11. The water uptake measurement system of claim 10, further comprising:
an insulating component that is connected to the sample chamber such that the heating element is positioned between the sample chamber and the insulating component.

12. A water uptake measurement system for measuring uptake of a fluid by a sample, comprising:
a sample chamber having an outer surface, an inner surface, an internal cavity, and a suspension aperture that is located at a first end of the sample chamber, wherein the suspension aperture extends from the outer surface of the sample chamber to the inner surface of the sample chamber, wherein the sample chamber includes a removable portion that is selectively separable from a base portion of the sample chamber;

a suspension component that passes through the suspension aperture of the sample chamber such that a first end of the suspension component is located outside of the internal cavity of the sample chamber and a second end of the suspension component is suspended within the internal cavity of the sample chamber, wherein the suspension component is configured to support the sample within the internal cavity such that the sample is spaced apart from the inner surface of the sample chamber; and a supply interface that is configured to deliver the fluid to the internal cavity of the sample chamber.

13. The water uptake measurement system of claim 12, wherein the removable portion of the sample chamber threadedly engages the base portion of the sample chamber.

14. The water uptake measurement system of claim 12, wherein the suspension aperture is defined through the removable portion of the sample chamber.

15. The water uptake measurement system of claim 12, further comprising:
a gasket that seals the removable portion of the sample chamber with respect to the base portion of the sample chamber when the removable portion of the sample chamber is in engagement with the base portion of the sample chamber.

* * * * *